United States Patent [19]

Eoga

[11] Patent Number: 4,540,504
[45] Date of Patent: * Sep. 10, 1985

[54] DENTURE CLEANER HAVING IMPROVED DISSOLUTION TIME AND CLARITY AND METHOD OF PREPARATION

[75] Inventor: Anthony B. J. Eoga, Boonton, N.J.

[73] Assignee: Warner-Lambert Company, Morris Plains, N.J.

[*] Notice: The portion of the term of this patent subsequent to Oct. 11, 2000 has been disclaimed.

[21] Appl. No.: 599,831

[22] Filed: Apr. 13, 1984

Related U.S. Application Data

[63] Continuation-in-part of Ser. No. 487,489, Apr. 22, 1983, Pat. No. 4,518,520.

[51] Int. Cl.$^3$ .............. C11D 7/18; C11D 7/30; C11D 7/56; C11D 17/00
[52] U.S. Cl. .............. 252/99; 252/102; 252/174; 252/174.16; 252/174.18; 252/174.19; 252/174.23; 252/350; 252/527
[58] Field of Search ............ 252/99, 174, 174.23, 252/186.3, 186.31, DIG. 2, DIG. 3; 264/117, 118, 120, 122, 127; 23/313 R

[56] References Cited

U.S. PATENT DOCUMENTS

| | | | |
|---|---|---|---|
| 4,115,519 | 9/1978 | Brichard | 423/279 |
| 4,405,486 | 9/1983 | Eoga | 252/186.31 |
| 4,409,118 | 10/1983 | Eoga | 252/99 |
| 4,422,950 | 12/1983 | Kemper | 252/186.38 |

*Primary Examiner*—Dennis L. Albrecht
*Attorney, Agent, or Firm*—Daniel A. Scola, Jr.; Gary M. Nath

[57] ABSTRACT

A cleansing composition is disclosed that is particularly suited for compaction into tablet form, and comprises a phosphate salt, an improved perborate salt mixture wherein the improvement comprises a combination of anhydrous perborate and monohydrate perborate in the amount of about 50% to about 70% by weight of the total cleansing composition, wherein the combination includes at least 20% by weight of the total cleansing composition of anhydrous perborate, said combination having a portion present in a compacted granulated mixture with from about 0.01% to about 0.70% by weight of said combination of a polymeric fluocarbon, and a chelating or sequestering agent present in amounts greater than about 10% by weight up to about 50% by weight of the total composition, said cleansing composition being capable of cleansing stained surfaces and the like with a soaking time of five minutes or less when dissolved in aqueous solution and producing a marked improvement in clarity of solution upon disintegration and cleaning efficacy over the prior art.

19 Claims, No Drawings

DENTURE CLEANER HAVING IMPROVED DISSOLUTION TIME AND CLARITY AND METHOD OF PREPARATION

The present application is a continuation-in-part of my copending application Ser. No. 487,489, filed Apr. 22, 1983 now U.S. Pat. No. 4,518,520.

The present invention relates generally to cleansing compositions, and more particularly to cleansing compositions that are prepared in tablet form for use.

Cleanser compositions, and in particular those compositions having utility for hard surface cleaning applications, have utilized oxidizing agents and bleaching agents in concert to remove visible stains, while at the same time providing the capability for the removal of scale or plaque buildup on the surfaces. Thus, a variety of cleansing compositions are known and have been prepared either with abrasive materials for use as scouring cleansers, or alone for purpose of mild surface cleaning applications such as passive dispersion in a liquid medium such as water, and for soaking applications, such as the cleaning of dentures. All of these compositions have employed a variety of sulfate salts, such as bisulfates, monopersulfates, and sulfates as detergents, oxidizers and the like, and have also utilized alkali metal and alkaline earth metal halides as bleaches. Such compositions have also included perborate, carbonate and phosphate salts in varying amounts, to provide effervescence and activation. Representative cleansing compositions covering these various applications are set forth in U.S. Pat. No. 3,337,466 to Puetzer et al., U.S. Pat. No. 3,704,227 to Hill, Applicant's U.S. Pat. No. 4,362,639 and Applicant's copending applications, Ser. Nos. 251,030, 380,157 and 380,104, all of which are incorporated herein by reference.

In the instance where the cleansing compositions mentioned above contain one or more perborate salts, and the compositions are prepared into tablets by compression, the compositions have presented certain drawbacks in that they are difficult to compress, and the resulting tablets lack mechanical strength. These problems are owing primarily to physical properties of the perborate salts employed. In particular, anhydrous sodium perborate, which has been utilized in the compositions in my copending applications, is commercially available as a fluffy powder having a low specific weight and density and therefore resistant to compaction and agglomeration. To a much lesser extent, this same difficulty is experienced with another perborate salt additive, sodium perborate monohydrate.

Prior attempts to remedy these deficiencies have focused upon the addition of greater amounts of standard tableting aids such as talc, sodium benzoate, and the like. The addition of greater amounts of these ingredients, however, while remedying the difficulties of initial processing and tablet formation, carry with them certain other drawbacks, namely that the formed tablets exhibit retarded action in use, that renders them less commercially desirable. In particular, the increased amounts of tableting aids tend to prolong the disintegration time of the tablet, with the result that the activity of the tablet is delayed and in some instances slightly suppressed, and therefore less attractive to potential consumers.

A process is disclosed in U.S. Pat. No. 4,115,519 to Brichard et al., for the manufacture of sodium perborate monohydrate, that purportedly results in the preparation of granules of the monohydrate possessing the desired particle size, specific weight, abrasion resistance and flowability sought for use in connection with the compaction of dental cleanser tablets. The technique disclosed by the patent, however, is complex and costly, and requires specialized apparatus to conduct a fluidized bed particle formation in contact with hydrogen peroxide. The patentees refer to prior art processes for the formation of the monohydrate salt, and indicates that those processes, as well, are complex and expensive, and frequently yield particles that are unsuitable for the present application.

U.S. Pat. No. 3,340,152, to Hotko, discloses that polyfluorocarbons may be utilized in the manufacture of tablets, as lubricants, and in amounts by weight of the tableting composition, ranging from about 1% to about 15% by weight, to supplant such known lubricants as magnesium stearate, sodium lauryl sulfate, polyethylene glycols and the like. Hotko suggests that the fluoropolymer may be added directly to the tableting mixture, in its capacity and amount as a lubricant, and purportedly has a favorable effect on the tablet-forming process. There is no disclosure in Hotko that the fluoropolymers would serve as agglomeration or compaction aids, to facilitate the preparation of granulated materials of increased and improved specific weight.

The applicant's previous applications have sought to overcome the traditional prior art problems involved in creating a tablet which maximizes hardness and mechanical integrity without unduly sacrificing dissolution time and cleansing speed and efficacy. Thus, in developing such a product there are numerous factors which must be considered and variation of any one yield compositions with different characteristics and hence different products.

The applicant's specific efforts have been devoted to creating a cleanser of improved after odor and tarnish resistance properties (U.S. Pat. No. 4,362,639) which employed as critical ingredients an oxidizing agent such as monopersulfate salt; a halide bleaching promoter, such as an alkali metal or alkaline earth metal; an effervescent compound, such as a perborate salt; and an ammonium ion contributor to inhibit the evolution of chlorine-like odor and taste. Additionally, the applicant has focused on making a smaller, lighter tablet which has equal or better dissolution times and cleaning efficacy as the prior art. Copending Application Ser. No. 380,157, filed May 20, 1982, U.S. Pat. No. 4,409,118, focused on a means of accomplishing this objective by forming a tablet which had good mechanical strength and excellent dissolution speed and cleansing efficacy. The addition of a polymeric fluorocarbon to a preformed granulated mixture of perborate salt allowed for improved compaction and dimensional stability without the tendency to stick to tablet forming equipment. The method of forming the granulated fluorocarbon-containing perborate salt mixture is described in copending Application Ser. No. 380,164 filed May 20, 1982, U.S. Pat. No. 4,405,486.

Heretofore the compositions of the prior art have not focused on a particular problem involving clarity which results when the combination of anhydrous perborate, monohydrate perborate and lubricity or compaction aids is used. Talc has in the past been used as a lubricant to increase workability and processing of the product and may aid in facilitating compaction to some extent. However, when combined with anhydrous perborate and monohydrate perborate, a cloudy solution results upon dissolution. The disadvantages of being an aesthetically unpleasing product upon commercial success are obvious.

Magnesium stearate has also been known for its lubricating properties when incorporated in cleansing powders or tablets, but products employing this type of compound suffer from prolonged dissolution times which are commercially unacceptable.

Cleanser compositions, and particularly denture cleanser compositions have heretofore not contained large amounts of chelating or sequestering agents because they interfered with the dissolution of tableted compositions, which in turn slowed down cleaning. If large amounts of sequestrants were mixed with sodium bicarbonate in a conventional prior art composition, the cleaning power and efficacy is not very good. This lack of efficacy is due to the lowering of the pH by the large amounts of the required sodium bicarbonate.

Great Britain Patent Application No. 2,095,694, published Oct. 6, 1982, concerns an effervescent denture cleanser composition containing an oxygen-releasing compound and a diphosphonic acid or its salt in amounts up to about 10% by weight. Acetyldiphosphonic acid, also known as ethane-1-hydroxy-1,1-diphosphonic salt and its alkali metal salts are preferred. This reference discloses that these phosphonic acid compounds are useful in removal of calcium phosphate-containing plaque, tartar and calculus on dentures at a pH of 10-12.

U.S. Pat. No. 4,409,118 discloses the use of chelators or sequestering agents in cleanser compositions in amounts up to about 30% by weight of the composition. The quaternary salt of ethylene diamine tetraacetic acid is disclosed. The purpose and function of these agents were for maintaining clarity of solution. This was possible since small quantities of the agents were used.

Another aspect of the instant invention is the incorporation of high levels of chelating or sequestering agents to assist in the removal of calcium deposits from stained surfaces. It has been discovered that the cleansing ability of the instant compositions is improved over the prior art through the incorporation of chelating or sequestering agents in amounts of up to about 50% by weight; and most preferably in amounts of about 25% to about 40% by weight of the total composition.

It is apparent that there exists a need for improved cleansing compositions, capable of being in powder or tablet form, which possess all the attributes of the prior art as well as improvements in tablet size, shape dissolution time, aesthetically pleasing solutions free of cloudiness and cleaning ability.

The combination of specific proportions of anhydrous perborate and monohydrate perborate salts has been found to produce an exceptionally clear solution upon addition of water when talc, magnesium stearate and lubricating aids of this sort are omitted from the composition. Additionally, the solutions are clear notwithstanding large amounts of chelating and sequestering agents being present.

In accordance with the present invention, a cleansing composition is prepared that is particularly suited for compression into tablet form, and which results upon dissolution in water an improved clarity of solution. Additionally, the speed of dissolution is improved resulting in better cleansing efficacy in substantially less soaking time.

Generally, the cleansing composition comprises a phosphate salt in an amount from about 20% to about 45% by weight, and a combination of an anhydrous perborate salt in the amount about 15% to about 45% and a monohydrate perborate salt in the amount of about 22% to about 45% by weight of the final composition. The proportion of anhydrous to monohydrate perborate should be about 1 to 3 to about 3 to 1 and preferably a propportion of about 1 to about 1, anhydrous to monohydrate perborate acid, and most preferably a proportion of about 1 to about 1.6. At least a portion of the perborate combination is present as a compacted, granulated mixture with from about 0.01% to about 0.70% by weight of the perborate combination, of a polymeric fluorocarbon. The amount of granulated mixture is not critical as long as it is an amount effective to facilitate tablet compaction, if tablet form is desired, without substantially sticking to tablet forming equipment and with suitable dimensional stability. Additionally, the granulated mixture must not be present in an amount such that it substantially interferes with dissolution time when placed in solution.

More particularly the instant invention's concerns are improved effervescent cleansing composition in tablet form comprising:

(a) about 20% to about 45% by weight of the final composition of a phosphate salt;
(b) an improved perborate salt mixture wherein the improvement comprises a combination of anhydrous perborate and monohydrate perborate in the amount of about 50% to about 70% by weight of the total cleansing composition, wherein the combination includes at least 20% by weight of the total cleansing composition of anhydrous perborate, said combination having a portion present in a compacted, granulated mixture with from about 0.01% to about 0.70% by weight of said combination of a polymeric fluorocarbon, said cleansing composition being capable of thoroughly cleansing stained surfaces within a soaking time of five minutes or less when dissolved in aqueous solution;
(c) a chelating or sequestering agent in amounts of greater than about 10% by weight up to about 50% by weight of the composition.

The mixture of the perborate salts and the polymeric fluorocarbon is prepared by compaction, such as by slugging or roller compaction, followed by comminution under agitation to form granules that may, for example, have a particle size whereby about 98% of the granules are capable of passing through a 20-30 mesh screen.

Preferably, the phosphate salt comprises an alkali metal phosphate, such as trisodium phosphate, present in an amount of from about 25% to about 40% by weight.

The perborate salts utilized in the present composition may comprise alkali metal perborates selected from the group consisting of alkaline metal perborate monohydrates and anhydrous alkali metal perborates. In particular, the sodium salts are contemplated, and the present compositions may contain from about 50% to about 70% by weight of the perborate salts.

Preferably, the compositions contained from about 50% to about 65% by weight of the perborate salts, including at least 20% by weight of the anhydrous alkali metal perborate.

The polymeric fluorocarbons is peferably present in an amount of from about 0.33% to about 0.66% by weight of the perborate salt, and may include at least one fluoroolefin.

Preferably, the polymeric fluorocarbon comprises polytetrafluoroethylene and the perborate salts of Sodium Perborate Monohydrate and Sodium Perborate Anhydrous in combination prepared in compacted, granular form comprises the combination of Anhydrous alkali metal perborate and the monohydrate alkali metal perborate.

The present cleansing compositions may also include other ingredients such as colorants, detergents, pH adjustment additives, perfumes and the like, and are particularly useful when prepared in tablet form for use, for example, as denture cleansers.

The present invention also relates to a method for preparing the effervescing cleansing composition, comprising preparing a perborate salt in a compacted, granular mixture with a polymeric fluorocarbon, in which the polymeric fluorocarbon is present in an amount by weight of the perborate salt, ranging from about 0.01% to about 0.70%, adding to the perborate salt a quantity of a phosphate salt whereby the phosphate salt is present in an amount by weight of the total composition of from about 20% to about 45%, and the perborate salt is present in an amount of at least 50% by weight, adding the chelating or sequestering agent in amounts of greater than about 10% by weight up to about 50% by weight, all to form a second mixture, and compacting the second mixture to form a plurality of tablets therefrom.

The perborate salt comprises a mixture of sodium perborate monohydrate and anhydrous sodium perborate, and the phosphate salt comprises trisodium phosphate, the particle size of which is such that about 100% shall pass through 20 mesh and less than about 20% through 100 mesh.

Accordingly, it is a principal object of the present invention to provide an effervescing cleanser composition capable of serving as a denture cleanser in tablet form or powder form, which when dissolved in solution yields a clear and aesthetically pleasing appearance. It is further object of the present invention to provide a cleanser composition as aforesaid, that is easily molded into tablets that retain their mechanical stability and strength.

It is a still further object of the present invention to provide a cleanser composition as aforesaid, that is promptly activated upon placement in water, whereupon total disintegration and dissolution time is improved.

It is still a further object of the present invention to provide a method for the preparation of the present cleansing compositions, which is simple and inexpensive.

Other objects and advantages will become apparent to those skilled in the art from a consideration of the ensuing detailed description.

The cleansing compositions of the present invention comprise a phosphate salt in an amount of from about 20% to show about 45% by weight. Preferably, the phosphate salt may be present in an amount ranging from about 25% to about 40% by weight, and comprises alkali metal phosphates and alkaline earth metal phosphates, with alkali metal phosphates preferred. More particularly, the alkali metal phosphate may comprise trisodium phosphate.

The phosphate component serves as a cleaner, and in the instance where the present compositions are utilized as denture cleansers, attacks and disintegrates the dental plaque that forms on the surface of the dentures. This cleaning role is in addition to the function of the phosphates as builders.

The instant compositions contain an anhydrous perborate salt in combination with a monohydrate perborate salt. The anhydrous perborate salt is present in the amount of at least about 20% by weight of the total composition and preferably in an amount from about 20% to about 25% by weight.

The perborate salts may be selected from alkali metal perborates and alkaline earth metal perborates, and more particularly may be selected from alkali metal perborate monohydrate and anhydrous alkali metal perborates. Thus, the sodium and potassium salts of the perborate monohydrate and anhydrous perborates may be utilized, and preferably, the perborate salts may comprise sodium perborate monohydrate and anhydrous sodium perborate. Also included are the Ammonium, Calcium and Magnesium salts of monohydrate and anhydrous perborates. Total perborate salt amounts are preferably in an amount ranging from 50% to about 70% by weight of the composition, and more preferably from about 50% to about 65% by weight.

The perborate salt functions in a variety of capacities within the present compositions, as it provides cleaning action, as well as promoting the activity of the compositions by initiating effervescence as well as inhibiting tarnish and corrosion of susceptible substrates immersed in solutions of the present composition.

A further feature of the present compositions, comprises the preparation of at least a portion of the perborate salt in a compacted, granulated mixture with from about 0.01% to about 0.70% by weight of the salt, of a polymeric fluorocarbon. The preparation of this compacted granular mixture and its employment in the present composition is particularly noteworthy, as it facilitates the compaction of the perborate salt without adversely effecting the properties and activity of tablets prepared from the composition. Perborate salts, and in particular, anhydrous sodium perborate, are extremely light, fluffy materials having a low specific weight, that have been difficult to compact when attempts to incorporate this material in denture cleanser tablets, for example, have been made. Thus, the combination of Sodium Perborate monohydrate and Anhydrous Sodium Perborate in the presence of the polymeric fluorocarbon has less of a tendency to stick to the tablet dies. The tablets prepared with the anhydrous perborate/monohydrate perborate combination are less frangible than the prior art compositions and therefore commercially more desirable. The said combination also leads to a tablet which dissolves completely and considerably faster than the tablets of the prior art. This codissolution feature, resulting from the anhydrous perborate/perborate monohydrate combination, increases the activity of the denture cleanser when placed in solution. The preparation of the pregranulation mixture also contributes to the final thickness of the tablet.

The harder the resultant slug the slower the disintegration of the tablet and the thinner the resultant tablet. Therefore, an appropriate hardness was selected which optimizes the rate of disintegration of the tablet as well as the hardness and thickness of the tablet.

Prior art attempts to remedy this deficiency by the addition of greater quantities of conventional tableting aids, have resulted in the preparation of tablets that, while dimensionally stable and mechanically strong, exhibit greatly diminished activity when placed in solution. Thus, distintegration times are undesirably prolonged, and in some instances distintegration does not take place.

The anhydrous sodium perborate is present in the optimized formula not only as an effervescence source but complements the function of the sodium monohydrate perborate by contributing, indirectly, to the rate of cleaning since the faster the tablet is dissolved the faster the rate of cleaning of the resultant solution.

Producing a tablet using Anhydrous Sodium Perborate and monohydrate perborate with the lubricating agents of the prior art yield cloudy, unacceptable solutions upon dissolution. The use of one of the perborates alone is not as effective as the combination in producing a product which has perceptibly enhanced effervescence with a rapid dissolution time. The instant invention optimizes the concept of the granulated fluorocarbon mixture of perborate salts through the selection of specific proportions of the anhydrous and monohydrate forms.

The instant compositions and tablets described herein are superior in efficacy than the prior art in removal of tobacco stains, food composites, and plaque. The efficacy of these compositions is of course a function of time, temperature and water volume used and as such comparisons must be based on amount of cleansing per a specific set of values for these factors.

The compositions of this invention have the added benefit that they can be made to be lighter in weight yet function as well and even superior to those tablets of the prior art which are heavier. This is presumably owed to the better compaction of the tablet, which in spite of its physical integrity and hardness, readily and rapidly distintegrates when placed in solution, releasing its active components for effervescence and cleansing.

Thus, another object of the instant invention is a composition which when formed into a tablet has a reduced weight without loss of efficacy.

As discussed earlier herein, U.S. Pat. No. 3,340,152 to Hotko, describes the use of a polymeric fluorocarbon as a lubricant in tablet formation. Efforts to utilize the polymeric fluorocarbons disclosed by Hotko within the ranges set forth in the patent, proved fruitless, as the resulting tablets, while dimensionally stable, exhibited little or no activity in solution. Likewise, efforts to place even reduced amounts of the polymeric fluorocarbons in direct combination with the ingredients of cleansers such as those presently disclosed, resulted in the preparation of tablets having similar drawbacks. Accordingly, the preparation of the perborate salts in the manner disclosed in the present invention is important to the preparation of compositions in tablet form, that possess the property of dimensional stability and ease of preparation, in combination with retention of desirable solution activity. Thus, tablets prepared by the present invention disintegrate as quickly, and in some instances more quickly than acceptable denture tablets prepared in accordance with the prior art.

The mixture of the perborate salts with the polymeric fluorocarbon may include the fluorocarbon in an amount preferably ranging from about 0.33% to about 0.66% by weight of the perborate salt. The polymeric fluorocarbon may be selected from a well know group of polymeric and copolymeric substances made up of carbon and fluorine, which, in addition, may contain hydrogen. The fluorocarbon may include at least one fluoroolefin; for example, polytetrafluoroethylene, copolymers of tetrafluoroethylene and hexafluoropropylene, and copolymers of vinylidene fluoride and hexafluoropropylene would be included. The preferred polymeric fluorocarbon comprise polytetrafluoroethylene.

The flurocarbon polymers may be utilized in the form of powders having particle sizes acceptable for combination with the perborate salts, and preferably ranging up to about 150 microns in size. The exact particle size of from about 25 to about 75 microns may be used. The exact particle size of the polymeric fluorocarbon is not critical to the practice of the present invention.

The preparation of the perborate salt-polymeric fluorocarbon mixture into compact granules may be conducted by compaction on a continuous or batch basis, by means, for example, of a roller compactor or a tablet slugging machine, to form a plurality of preforms such as flakes or slugs. Preforms would thereafter be subjected to comminuition undr agitation to form the desired particles, and may possess particle sizes ranging on the order of 30 mesh or greater. The exact details of the preparation of the compacted perborate salt particles is disclosed in my copending Application Ser. No. 380,164, the disclosure of which is incorporated herein by reference.

In addition to the ingredients set forth above, the present compositions may contain a variety of additional ingredients selected on the basis of desired end use. Thus, for example, the compositions may include detergent compounds, such as organic and inorganic detergents, including non-ionic detergents such as the various polyoxyethylene ethers of aromatic and aliphatic alcohols, as well as the polyoxyethylene ethers of hydrophobic propylene oxide polymers. These compounds assist in maintaining a foaming action, in the instance where the cleansing compositions are placed in aqueous solution.

Also, the compositions may contain other adjuvant materials, that may be inorganic or organic in structure. Thus, inorganic water-soluble alkaline builders such as alkali and alkaline earth metal carbonates, hydroxides, and mixtures may be added.

The present compositions may optionally contain sequestrants for the purpose of maintaining solution clarity, in the instance where the compositions are placed in solution. The sequestrants may also assist in the inhibition of corrosion and tarnish of particles soaked in solutions containing the present compositions. Useful sequestrants include ethylene diamine tetracetic acid (EDTA) and its corresponding alkali salts, as well as other polyfunctional organic acids, such as citric acid, maleic acid and their corresponding salts.

Those chelating or sequestering agents which are to be used in amounts greater than about 10% up to about 50% by weight are phosphonic acid and its derivatives, and carboxylic acid derivatives. Among those specific phosphonic acid derivatives are the salts of ethane-1-hydroxy-1,1-diphosphonic acid. For example, aminotri(methylene phosphonic acid), 1-hydroxyethylidene-1,1-diphosphonic acid, ethylenediamine tetra(methylene phosphonic acid), ethylenediaminetetra(methylene phosphonic acid), hexamethylenediaminetetra(methylenephosphonic acid), diethylene triamine penta(methylenephosphonic acid), among others. The alkali metal salts and analogues of the above phosphonates are also useful.

Those carboxylic acid derivatives useful as chelating or sequestering agents include the hydroxycarboxylic acids and salts thereof, as well as amino carboxylates. For example, the hydroxycarboxylic acid compounds include gluconic acid and citric acid, among others known in the art. The amino carboxylates include nitriloacetic acid and ethylenediaminetetraacetic acid (EDTA). As previously mentioned, however, small amounts of EDTA are not effective in removal of calcium deposits from stained materials.

Mixtures of any or all of the chelating or sequestering agents is also contemplated.

Thus, the instant invention requires a critical combination of a phosphate salt, a pregranulated perborate salt mixture, and a chelating or sequestering agent in amounts greater than about 10% up to about 50% by weight of the composition. The pregranulation and method of tableting of the instant invention permit the high percentages of chelating or sequestering agents to be incorporated without experiencing cloudiness of solution or a significant change in tablet dissolution time.

In the instance where the composition is to be prepared for use as a denture cleanser, other additives such as flavorings, colorants, perfumes and the like may be added in various amounts, as mentioned earlier. For example, the flavorings may include varieties of mint, oil of clove, artificial vanilla flavoring, and others. These materials may be included and blended in various combinations within the scope of the present invention. The choice of the required amounts is likewise within the skill of the art.

In the instance where the present cleansing compositions are formulated for use as denture cleansers, the colorants useful herein are those known as F.D. & C. & D. & C. dyes and lakes. These materials are certified by the Federal Food and Drug Administration as acceptable for use in food, drug and cosmetic applications, and drug and cosmetic colorings. The materials acceptable for the foregoing spectrum of use are preferably water-soluble, and include indigoid dye, known as F.D. & C. Blue No. 2, or its Lake which is the disodium salt of 5,5'-indigo-tindisulfonic acid. Similarly, the dye known as F.D. & C. Green No. 1, comprises a triphenylmethane dye or F.D. & C. Green #3 and is the monosodium salt of 4-[4-(N-ethyl-p-sulfobenzylamino)diphenylmethylene]-[1-(N-ethyl-N-p-sulfoniumbenzyl)-2,5-cyclohexadienimine] or F.D. & C. Green #3. A full recitation of all F.D. & C. and D. & C. and their corresponding chemical structures may be found in the Kirk-Othmer Encyclopedia of Chemical Technology, at Volume 5, pages 857–884, which text is accordingly incorporated herein by reference. Dyes and colorants will fade at different rates and may be chosen to provide specific end points.

The foregoing colorants may be blended with each other in a variety of combinations. It is particularly desirable that the colorants be chosen so that the composition when initially dissolved will present a deep hue. This is important in the instance where the composition serves as a denture cleanser, as the fading phenonmenon embodied in denture cleansers can be more easily observed by the end user.

The use of F.D. & C. Blue #1 Lake is particularly important in that the tablet color is blue without adversely affecting the color of the solution.

The present invention includes a method for the preparation of salts containing the hydrogen peroxide by crystallization of the hydrated and non-hydrated salts, which comprises preparing at least a portion of the combination of at least two of the perborate salts components, said combination comprising an anhydrous and a monohydrate perborate salt as a first pregranulation (pregranulation A) including the polymeric fluorocarbon, and compacting this first mixture to form a plurality of particles thereof. In a similar manner a second type of pregranulation can be formed (pregranulation B) comprising at least a portion of the phosphate, the chelating or sequestering agent, a detergent and the polymeric fluorocarbon, and compacting the second mixture to form a plurality of particles thereof. The pregranulation mixtures, A and B, should be in combination. The remainder of the ingredients, including the phosphates purchased or prepared with a particle size within the aforementioned ranges, are then combined to form a final mixture which may be prepared in tablet form, in the instance, for example, where the present compositions are to be utilized as denture cleansers. The present invention relates to the said cleansing composition as a fast acting denture cleanser and a method of preparation of a superior denture cleanser which results in an improved clarity of solution when dissolved in water and a process for producing the same in a solid dosage form The use of finely divided polytetrafluoroethylene and a high foaming surfactant results in improved aesthetics. This is due to the fact that the majority of the Polytetrafluoroethylene becomes trapped in the foam layer thereby aggregating at the surface of the aqueous solution and leaving the volume of the solution clear of particles. The polytetrafluoroethylene in combination with the perborate combination described above are believed primarily responsible for the improved properties of the instant compositions.

It is preferable to prepare the present compositions in tablet form in such instance, as it is easier to achieve the uniformity of quantity and distribution of the ingredients of the compositions that is necessary to assure the corresponding uniformity of performance of the cleanser. Thus, cleanser tablets have been found to exhibit uniformity of color reaction, distintegration and fade time, in cleaning ability on a tablet-to-tablet basis.

In accordance with the present invention, the compositions may be prepared in tablet form without the need for increased addition of ingredients such as excipients, tableting agents and the like. While such ingredients may be added, the amounts of these ingredients may be reduced, due to the favorable effect exerted by the polymeric fluorocarbon present in the compacted granules of the perborate salt. Naturally, minor additional quantities of ingredients such as the polymeric fluorocarbon, may be made for their stated purpose, such as for lubrication and the like, however such additions and their respective amounts are not critical and do not form a part of the present invention.

A fuller understanding of the present invention will be gained from a review of the following illustrative examples. Unless specified otherwise, all amounts expressed as percent, are intended to be a percent by weight of the total composition. These examples are not intended to limit the effective scope of the invention.

EXAMPLES I–IV

A series of cleanser compositions were prepared having the ingredients set forth in Table I, below.

The compositions of each of Examples I–IV were prepared as follows. Initially, a quantity of anhydrous sodium perborate, in the form of a fluffy powder, and sodium perborate monohydrate was combined in a container with a quantity of polytetrafluoroethylene powder identified as Grade F5A by Allied Chemical Corp.

The polytetrafluoroethylene was added in the amounts based upon the weight of the perborate, as indicated with respect to each of the examples, above. Blending was performed for about 3 minutes, after which the mixture was compressed by passing through a tablet slugging machine having 27/32" dies. The slugs were then passed through an oscillating granulator having a 16 mesh screen, to form the granules of the anhydrous perborate/polytetrafluoroethylene/sodium perborate monohydrate mixture.

The remaining ingredients of the composition were added to the perborate, the phosphate being added first, to form the second mixture, after which the mixture was formed into tablets by compression in a tablet slugging machine having a tablet die of 26/32". The tablets were performed to a hardness ranging from about 20 to about 30 S.C.U., and were thereafter cured in a hot air oven for 45 minutes at 95° C.

After the preparation of the tablets was complete, representative tablets from each of the four formulations were tested for activity and efficacy, by placement in individual containers having approximately 120 milliliters of water at 45° C.

Each of the compositions tested, exhibited a disintegration time of approximately 90 seconds or less, a pH ranging up to about 11.2, and a fade time of approximately 5 minutes. A reduced form tablet weight would fade in 12 minutes. It was determined that each of the compositions could thus be prepared into tablets for use as denture cleansers, with satisfactory activity and efficacy.

TABLE I

| Ingredients | \multicolumn{4}{c}{Examples Percent Weight/Weight of the Total Composition} | | | |
|---|---|---|---|---|
| | I | II | III | IV** |
| Sodium Bicarbonate | — | 14.0 | — | Reduced weight of Example I 88% w/w |
| Citric Acid | — | 10.3 | — | |
| Sodium Carbonate | — | 12.8 | — | |
| Colorant | 0.2 | 0.1 | 0.25 | 0.18 |
| Oxone | — | 39.5 | — | — |
| Ethylene Diamine Tetraacetic Acid Tetrasodium | 3.4 | 1.25 | 2.7 | 3.00 |
| Flavor and Fragrance | 0.5 | 1.0 | 0.53 | 0.44 |
| Detergent | 0.5 | 0.65 | 0.17 | 0.44 |
| Magnesium Stearate | — | 0.2 | 0.02 | — |
| Sodium Perborate Monohydrate | 37.3* | 12.5 | 33.7 | 32.80 |
| Anhydrous Sodium Perborate | 22.85* | — | 20.0* | 20.10 |
| Trisodium Phosphate | 33.8 | — | 24.6 | 29.70 |
| Sodium Benzoate | 1.0 | 1.6 | 1.1 | 0.88 |
| Polytetrafluoroethylene | 0.45 | — | 0.23 | 0.40 |
| Filler | — | 6.1 | — | — |
| Sodium Meta Silicate | — | — | 16.7 | — |

*Includes approximately 0.45% by weight of total perborate polytetrafluoroethylene prepared as a granulated mixture.
**This example is based on 88 grams total weight.

Example I represents a preferred composition of the instant invention. Example II represents a typical composition of the prior art. Example III is nearly identical to Example I except that sodium meta silicate and magnesium stearate are added. As previously discussed above, magnesium stearate is used as a lubricant to facilitate preparation of the composition, making it easy to work and form. Sodium meta silicate is used in the prior art primarily as a cleanser. There are disadvantages to using silicates, particularly meta silicates, because they tend to increase the pH of the solution upon tablet dissolution. The increase in pH is believed to increase the darkness of the color of certain stains on dentures, thereby defeating the purpose of the product. Additionally, magnesium silicate contributes to tablet production problems by causing the formed tablet to adhere to the punches or dies. Thus, if the prior art compositions required the cleansing power of the silicate, it was advisable to have a lubricant, such as magnesium stearate, also present to prevent the production problems of adherence to dies or punches.

Example IV is identical in ingredients to Example I but the tablet is reduced in weight by 88%. The percents reported under this example are based on a total of 88 grams.

TABLE II

| Ingredients | % weight/weight of the Total Composition | |
|---|---|---|
| | V | VI |
| Sodium Perborate Monohydrate | 36.3 | 36.3 |
| Sodium Perborate Anhydrous | 22.3 | 22.3 |
| Ethylenediaminetetraacetic Acid Tetrasodium Salt Dihydrate | 39.2 | — |
| Ethylenediamine tetra (methylene phosphonic acid) | — | 39.2 |
| Fragrance | 0.7 | 0.7 |
| Surfactant | 0.7 | 0.7 |
| Polytetrafluoroethylene Powder | 0.6 | 0.6 |
| Color | 0.1 | 0.1 |
| Lubricating Aids | 0.025 | 0.025 |

Examples V and VI represent compositions of the instant invention which contain large amounts of the chelating agents ethylenediamine tetraacetic acid tetrasodium salt dihydrate and ethylene diamine tetra (methylene phosphonic acid). These agents were added in these amounts to demonstrate improved efficacy of cleaning and particularly the removal of calcium deposits on stained surfaces.

IN VITRO TESTS

In vitro tests were performed on stained tiles and each of the compositions in Examples I-IV in Table I and Examples V and VI of Table II were used in tablet form to compare efficacy of cleaning. The compositions were tested for removal of composite food, plaque stain and tobacco stain on denture tiles.

The composition of Example I, embodying the instant invention, was found to be equivalent to Example III in removal of food and stain from denture test tiles. This would be expected since there is very little variation of the compositions, and indicates that magnesium stearate and sodium meta silicate are not necessary to the instant composition.

The composition of Example I was superior to Example II in removal of plaque and stain on tiles in a period of 5 minutes and was surprisingly superior in clarity upon completion of dissolution as well. The composition of the prior art (Example II) required 12 minutes to equal the efficacy and cleaning capability of Example I and yielded a less aesthetically pleasing and clear solution. The reduced weight composition of Example IV was found to be equivalent and sometimes superior to the composition of Example II when tested on stained tiles for 12 minutes. The significance of this relates to a considerable cost savings, since a lighter product can be made which has the same cleansing power and efficacy as the heavier tablet of the prior art in the same cleaning time; or a standard weight tablet can be made which cleans as well as the prior art in half the soaking time without cloudiness.

The preferred compositions of Examples V and VI, containing 39% of the chelating agents, were more effective at removing the plaque and stains and particularly the calcium deposits from the tiles than the composition of Example I. This demonstrates that the high percentages of chelating agents are effective at improving the cleaning ability of the instant compositions. No cloudiness or change in dissolution time was distinguishable between Examples I, V and VI.

The in vitro tests above indicate several facets of the instant invention. One such facet concerns the speed of cleaning of the instant compositions over the prior art while simultaneously producing an improved clarity of solution. Another facet concerns maintaining the cleansing speed and efficacy equivalent to or slightly better than the prior art, yet having substantially reduced tablet weight and size and ingredient amounts in accomplishing this.

CLINICAL TESTS

Clinical tests were performed on forty visibly stained dentures obtained from subjects who had restricted their oral hygiene practices and exposed their dentures to exaggerated quantities of tea, coffee, blueberries, and grape juice. The dentures were constructed of ADA certified materials and subjects refrained from cleaning their dentures for a total period of eight days prior to test using a specified procedure for consuming the staining foods. One half of each denture, as determined randomly, was cleaned with the prior art composition, Example II, for 12 minutes by soaking in aqueous solution, and the other half of the denture was cleaned in the same manner using the instant composition, Example I, in aqueous solution for 5 minutes of soaking time. The dentures were then examined and rated by an expert panel to determine which half of the denture was cleaner. Following the overall examination, the cleanliness of specified interproximal spaces was evaluated. In order to establish intra-examiner reliability, the dentures were randomly rearranged and evaluated a second time. The judges were not aware of the treatment regimen and made their own independent observations and judgment. Statistical analysis was conducted on the clinical study. The study was designed so that each denture surface received a total of eight ratings (two evaluations per denture by each of the four judges).

The design of this study provided for an actual in-use denture staining and cleaning. Restricted oral hygiene practices by the test subjects as well as the exposure to exaggerated staining mediums produced a visible stain on the dentures which was subsequently cleaned with the prior art composition (Example II above) under controlled conditions of temperature and time.

The results of the study clearly showed that the instant compositions are equally efficacious in less than half the soaking time than the prior art compositions in the overall removal of composite food stains from denture surfaces and in removal of composite stains from interproximal spaces. More particularly, the above study showed the instant applications when formulated into tablet form are equal or better in efficacy in a 5 minute soaking time than a tablet of the prior art in a 12 minute soaking time.

This invention may be embodied in other forms or carried out in other ways without departing from the spirit or essential characteristics thereof. The present disclosure is therefore to be considered as in all respects illustrative and not restrictive, the scope of the invention being indicated by the appended claims and all changes which come within the meaning and range of equivalency are intended to be embraced therein.

What is claimed is:

1. An improved effervescent cleansing composition in tablet form comprising:
   (a) about 20% to about 45% by weight of the final composition of an alkali metal or alkaline earth metal phosphate salt;
   (b) an improved perborate salt mixture wherein the improvement comprises a combination of anhydrous perborate and monohydrate perborate in the amount of about 50% to about 70% by weight of the total cleansing composition, wherein the combination includes at least 20% by weight of the total cleansing composition of anhydrous perborate, wherein the proportion of anhydrous to monohydrate perborate is from about 1 to 3 to about 3 to 1, said combination having a portion present in a compacted, granulated mixture with from about 0.01% to about 0.70% by weight of said combination of a polymeric fluorocarbon, said cleansing composition being capable of thoroughly cleansing stained surfaces within a soaking time of five minutes or less when dissolved in aqueous solution;
   (c) a sequestering agent in amounts of greater than about 10% by weight up to about 50% by weight of the composition, said sequestering agent being selected from the group consisting of phosphonic acid derivatives, carboxylic acid derivatives and mixtures thereof.

2. The composition of claim 1 wherein said phosphate salt comprises trisodium phosphate.

3. The composition of claim 1 wherein said perborate salt mixture comprises alkali metal and alkaline earth metal perborates.

4. The composition of claim 3 wherein said alkali metal perborate salt mixture comprises sodium perborate monohydrate and anhydrous sodium perborate.

5. The composition of claim 1 wherein said anhydrous perborate is present in an amount of from about 20% to about 25% by weight.

6. The composition of claim 5 wherein said anhydrous perborate comprises anhydrous sodium perborate.

7. The composition of claim 1 wherein said polymeric fluorocarbon includes at least one fluroolefin.

8. The composition of claim 7 wherein said polymeric fluorocarbon comprises polytetrafluoroethylene.

9. The composition of claim 8 wherein said polymeric fluorocarbon is present in an amount from about 0.33% to about 0.66% by weight.

10. The composition of claim 1 further including at least one material selected from the following: builders, detergents, lubricants, perfumes, flavorings, excipients, disintegrants, and mixtures thereof.

11. The composition of claim 1 wherein the sequestrant is selected from the group consisting of amino carboxylate, hydroxycarboxylate and mixtures thereof, present in amounts of greater than about 10% up to about 50% by weight of the composition.

12. The composition of claim 11 wherein the sequestrant comprises ethylenediamine tetraacetric acid or nitrilotriacetic acid and salts thereof.

13. The composition of claim 11 wherein the sequestrant is selected from the group consisting of gluconic acid, citric acid and salts thereof.

14. The composition of claim 13 wherein the sequestrant comprises a phosphonate salt, its alkali metal salts and mixtures thereof present in amounts of greater than about 10% up to about 50% by weight of the composition.

15. The composition of claim 14 wherein the sequestrant is selected from the group consisting of amino tri(methylenephosphonic acid), 1-hydroxyethylidene-1,1-diphosphonic acid, ethylenediamine tetra(methylene phosphonic acid), hexamethylenediaminetetra(methylenephosphonic acid), diethylene triamine penta(methylenephosphonic acid) and mixtures thereof.

16. The tablet of claim 1 useful as a denture cleanser comprising the composition of claim 1.

17. The tablet of claim 1 useful as a denture cleanser comprising the composition of claim 6.

18. The tablet of claim 1 useful as a denture cleanser comprising the composition of claim 9.

19. The tablet of claim 1 useful as a denture cleanser comprising the composition of claim 15.

* * * * *